United States Patent [19]
Lukesch

[11] 3,991,472
[45] Nov. 16, 1976

[54] DENTURE

[76] Inventor: Friedrich Lukesch, Ernest Thun Strasse 9, Salzburg, Austria, A-5020

[22] Filed: Aug. 4, 1975

[21] Appl. No.: 601,338

[30] Foreign Application Priority Data

Aug. 12, 1974 Austria .............................. 6601/74

[52] U.S. Cl. .................................................... 32/9
[51] Int. Cl.² ....................................... A61C 13/00
[58] Field of Search ................ 32/2, 8, 9, 10 R, 12

[56] References Cited
UNITED STATES PATENTS

| | | | |
|---|---|---|---|
| 2,854,746 | 10/1958 | Lester et al. ............................. | 32/2 |
| 2,866,285 | 12/1958 | Gerber .................................... | 32/9 |
| 3,328,879 | 7/1967 | Bax ......................................... | 32/12 |

Primary Examiner—Louis G. Mancene
Assistant Examiner—Jack Q. Lever
Attorney, Agent, or Firm—McGlew and Tuttle

[57] ABSTRACT

The denture construction for anchoring an artificial tooth in a person's mouth comprises an anchoring member which is adapted to be fixed in the mouth and which has a bore therethrough with an intermediate small diameter bore portion and an outwardly tapered bore portion on each end. The substantially cylindrical pin having an outer edge which is threaded into a U-shaped plate which is affixed to a recess in the bottom surface of an artificial tooth, has an intermediate small diameter pin bore and the bore is widened outwardly toward each end. The end of the pin which is not affixed to the tooth plate is advantageously spherically formed and has a wider end than the small diameter bore portion. The pin is provided with a transverse slot to permit the portions on each side of the slot to be sprung together so as to permit the pin to be inserted through the small diameter bore portion of the anchoring member. Exterior surfaces on each end of both the anchoring member and the pin are advantageously spherically formed so as to permit smooth rolling engagement between the parts when the tooth is subjected to stresses which would place the surface of the pin in contact with a surface of the anchoring member.

7 Claims, 5 Drawing Figures

DENTURE

The invention relates to a denture with at least one anchoring which can be fixed, e.g., on an anchor-tooth and which is provided with a bore into which latter a fastening element with preferably crosswise arranged longitudinal slots and a recess can be snapped in whereby the diameter of said fastening element for an artificial tooth is longer than that of the bore.

Dentures of that kind are known and produced in different embodiments. One conventional denture, e.g., is provided with conical holding elements which are resilient because of the arrangement of crossed longitudinal slots, whereby the holding elements are snapped in an anchoring with conical recesses. In the upper end of the holding part a flange-like projection is provided to lie close to the upper edge of the anchoring. In order to avoid that chewing causes an unevenly distributed strain of the anchor-tooth either because of free end dentures or because of paradentosis, the upper edge of the anchoring is sloped downwards from its connection with the anchoring tooth, thus realizing a certain flexibility of the artificial teeth.

A further conventional denture is also provided with conically converging holding parts which are resilient because of a longitudinal slot and have widened insertionends which are inserted into a rectangular recess of an anchoring. The anchoring is provided with a flange on its lower end over which flange the thick end of the holding plate snaps in. On the upper end of the holding part a holding plate which carries the artificial tooth is provided to have two humps that rest on the anchoring. In order to avoid the unequal strains which occur with free end dentures one of said humps may be removed, thus causing a further flexibility of the artificial tooth in one direction.

In another conventional denture the anchoring has a cylindric bore with enlarged ends. The holding part has a cylindric pin with a thicker end which snaps in the lower enlarged part of the bore. In this case the holding part cannot be moved.

Practical testing of these conventional embodiments has shown, however, that they do not come up but to a very small extent to the exigences. The sloping of the upper edge resp. the removal of one of the humps of the holding plate makes the artificial teeth flexible in one direction, but due to the fact that the holding part rests on the anchoring in the area of the anchor-tooth this causes only an insignificant reduction of the strains effective on the anchoring. Therefore the teeth tend towards bending into the longitudinal direction of the anchoring, thus causing a pressure on its upper end and a tension on its lower end, which forces eventually lead towards a damaging of the denture, an involution of the gums and finally a loosening of the anchor-tooth.

The forces which become effective on the tooth during chewing are not only vertical with respect to the tooth, as scientific and geometric studies of the chewing function have revealed. Actually the forces which are effective on the teeth may have different directions as well as different strengths.

In conventional dentures these different strains can, however, not be levelled out, which means that a damaging of the dentures as well as unnaturual strains on the jaw-joint and on the anchor-tooth may occur. Thus, e.g., in dentures like those described, in which a flexibility of the teeth is given only in one direction, the strain on the anchor-tooth is decreased, while, however, the strain on the jaw-joint is increased.

Therefore the object of the invention was to create a denture which is fixed, e.g., to an anchor-tooth in a way as not visible from outsides, whereby the anchor tooth is preferably provided with a crown, an inlay or a root-cap, and whereby the denture receives the chewing forces effective on it in a possibly natural way without inhibiting the bio-mechanical function of the jaw-joint.

According to the invention this is achieved by the fact that a denture of the type described in the beginning is provided with a bore that is widened at its two ends, whereby at least the one of the widened ends which is directed towards the artificial tooth, preferably, however both the widened ends, has (have) curved concave, preferably spherically shaped surfaces in the longitudinal direction of the bore, which surfaces carry the fastening element represented by a conventional, substancially cylindric pin, the recess in the longitudinal direction of the pin having curved convex surfaces which are also preferably spherically shaped.

In this case the bearing of the fastening elements in the anchoring corresponds with the latest results of research work in the field of gnathology. For this end the anchoring has upper surfaces whose form is similar to that of the socket of the jaw-joint or also to the chewing surface of a natural tooth of the lower jaw. Accordingly, the fastening element which snaps in the anchoring is also provided with outer surfaces that correspond with the head of the jaw-joint resp. with the chewing surface of a natural tooth of the upper jaw. The invention represents a closing of the gap which exists in dentures between the biomechanically correct formation of the flexible parts between the chewing surfaces of the teeth and the joint surfaces of the jaw joints, on which parts the chewing forces become effective. Therefore the denture according to the invention does not only prevent an abnormal wear and tear of the artificial as well as of the possibly still existing natural teeth, but avoids also an unnatural and often painful strain on the jaw-joint.

Like with conventional dentures, it is also possible with dentures according to the invention to arrange the recess in the lower part of the cylindric pin. Therefore the cylindric pin does preferably not project below the under edge of the anchoring, which fact avoids negative effects in the denture's zone of contact with the rim of the jaw.

In one embodiment the part of the cylindric pin which is directed away from the artificial tooth may have a smaller diameter than the part directed towards the artificial tooth.

In a preferred embodiment it is furthermore provided that all the curved surfaces have the same radius of curvature. In case the artificial tooth, i.e. the cylindric pin, is pressed into a direction other than vertical the cylindric pin can move within the anchoring in a way very similar to a ball joint resp. the jaw-joint, whereby a close contact is maintained between the outer surface of the cylindric pin and the inner surface of the enlarged part of the bore of the anchoring.

The enlarged part of the bore which is directed away from the artificial tooth may extend until about the point of contact between the anchoring and the cylindric pin.

In the following the invention is described in detail with reference to the figures of the attached drawing, without, however, being limited to this embodiment.

Figure 4A:
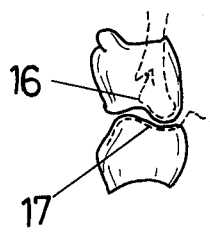
Figure 4B:
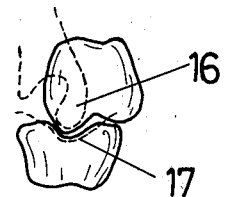

The particular parts of the denture in the embodiment are a cylindric pin 12 the upper end of which is provided with a thread 2. The part of the pin 12 which snaps in the anchoring 13 has a recess 7, whereby the curved surfaces 8, 8' of this recess 7 are represented by sperical convex surfaces which correspond with the round head of the jaw-joint represented in the FIG. 4 A and 4 B. A plate 1 carrying the artificial tooth 15 and strutting against the jaw over a medium 10 of elastic material is screwed onto the cylindric pin 12. The cylindric pin 12 is provided with longitudinal slots 14 which are arranged cross-wise, and on its far end with respect to the artificial tooth it is sloped in order to permit an easier insertion of the pin 12 into the anchoring 13.

Figure 1:
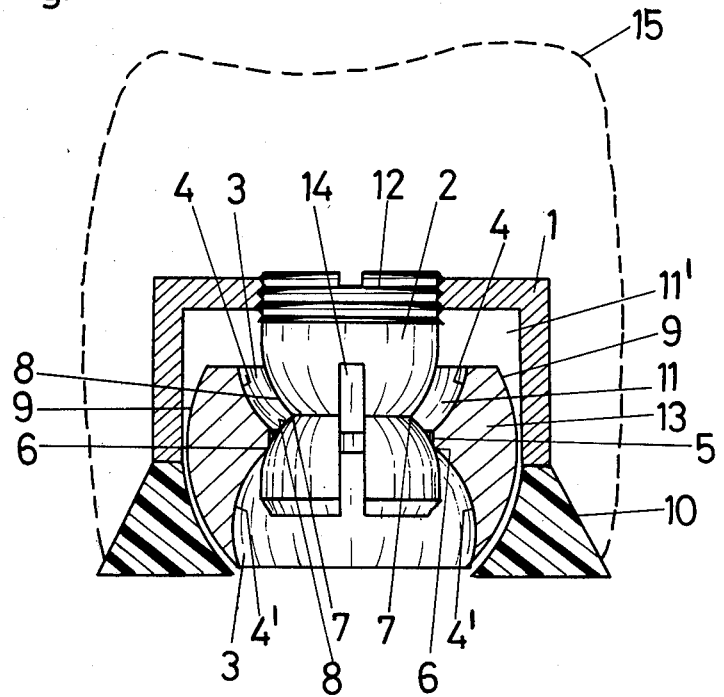
FIG. 1 is a section of a denture according to the invention in a transverse direction with respect to the jaw, whereby no forces are effective on the denture.
Figure 2:
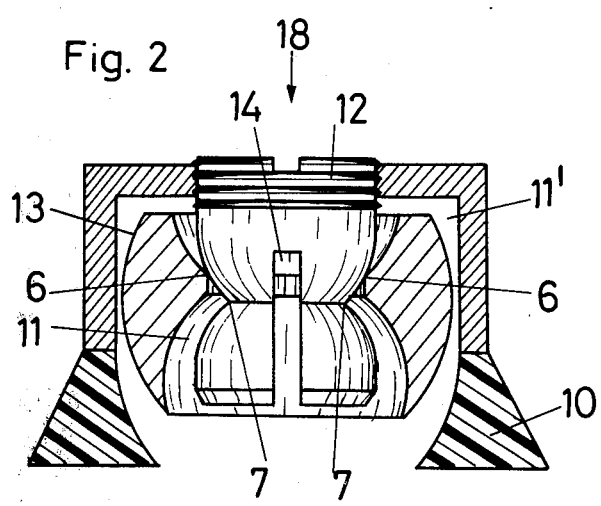
FIG. 2 is a section according to the one shown in FIG. 1, whereby a regularly distributed force is effective.
Figure 3:
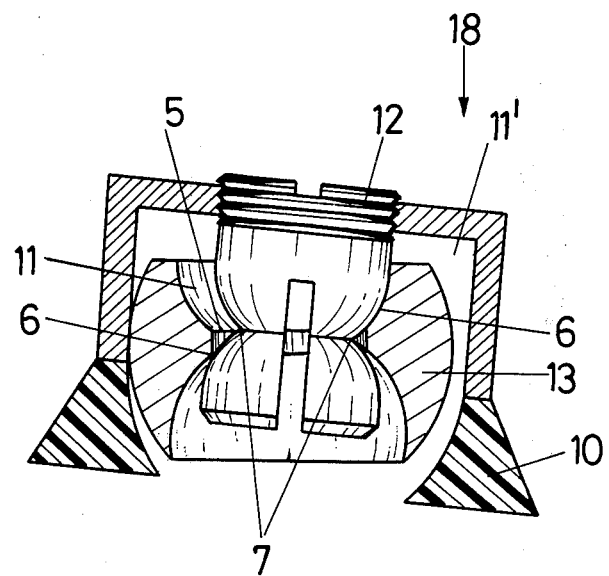
FIG. 3 is a section of a further embodiment similar to FIG. 1 with a unilateral force being effective on the denture, and FIG. 4 A and 4 B are schematical representations of the biomechanically correct position of the jaw-joint resp. the corresponding form of the chewing surfaces of the teeth in order to make clear the object of the invention.

The anchoring 13 is provided with a cylindric bore 5 which, in the embodiment, does only appear in a small section representing the zone of contact 6 between the anchoring 13 and the cylindric pin 12. The two ends of the bore 5 are provided with enlarged parts 3, 3' which have spherical surfaces as can be seen from the FIG. 1 and 2. In this case the enlarged part 3 corresponds to the socket 17 of the jaw joint as represented in the FIG. 4 A and 4 B. It is, however, also conceivable, to make the enlarged part 3 in a way that its curved surface 4 has the same radius of curvature as the curved surface 8 of the cylindric pin 12 in order to have a close contact of these two surfaces, even in case the strains effective on the denture are one-sided (FIG. 3).

For reasons of a facilitated production it is preferable that all the curved surfaces (8, 8', 4, 4') have the same radius of curvature. It is, however, also conceivable to choose different radii for the surfaces 4' and 8', and for the surfaces 4 and 8, respectively.

The diameter of the bore 5 of the anchoring 13 is smaller than that of the cylindric pin 12, which fact entails that an undesired loosening of the artificial tooth after the snapping in of the cylindric pin is impossible. Furthermore the diameter of the cylindric pin 12 is smaller than that of the enlarged parts 3 and 3' and the diameter of the narrowest part of the pin 12 (at the recess 7) is also smaller than that of the bore 5, i.e. the necessary functioning space 11 for the movement of the artificial tooth 15 is provided at all sides.

The outer surfaces 9 of the anchoring 13 are preferably also curved in order to provide the necessary free moving space 11' also in this area.

In case no forces are effective on the tooth (FIG. 1) the cylindric pin 12 is snapped in the anchoring 13 and is held in the represented position by the elastic medium 10 which is in contact with the gums.

In case there are forces effective on the denture (FIG. 2 and 3) the cylindric pin 12 yields to the occuring pressure in the direction of fleche 18 and slides into the upper enlarged part 3 in a way that even irregular chewing forces do not cause negative effects on the gums or on the jaw and the jaw-joint respectively. In case the effective forces are stopped the cylindric pin 12 slides back into its resting position (FIG. 1) because it is brought into this position by the elastic medium 10 and by the resilience of the gums.

The fastening element does not project below the under edge of the anchoring, even in case forces are effective on the artificial tooth, therefore there are no direct pressures that might become effective on the gums.

The denture according to the invention may be executed as a single artificial tooth fastened to an anchor-tooth, it may, however, also be represented by a chewing bar which is, e.g. fastened between two anchoring teeth, wherein the chewing bar is represented by the anchoring 13 in corresponding intervals.

What is claimed is:

1. A denture construction for anchoring an artificial tooth in a person's mouth, comprising an anchoring member adapted to be fixed in the mouth and having a bore therethrough with an intermediate small diameter bore portion and an outwardly tapered bore portion on each end of the small diameter bore portion, a substantially cylindrical pin having an outer end with securing means for fixing the pin to an artificial tooth and having an intermediate small diameter pin portion and being widened outwardly toward each end, said pin having an inner end opposite to said outer end which is wider than said small diameter bore portion and having a slot therethrough adjacent said inner end permitting portions on each side of the slot to be sprung together to permit the inner end to be engaged into said anchoring member beyond the small diameter bore portion.

2. A denture according to claim 1, wherein the outwardly tapered bore portions of said anchoring member and the outwardly widened portions of said pin being curved complementarily so as to facilitate sliding interengagement between said pin and the surface bounding the tapered bore portion of said anchoring member.

3. A denture according to claim 2, wherein the outer end of said pin is of a smaller diameter than the inner end.

4. A denture according to claim 2, wherein the curved surfaces of said pin and said anchoring member bore all have the same radius of curvature.

5. A denture according to claim 1, wherein the inner end of said pin would engage with the tooth in a substantially vertical position as a portion which comes into contact with the small diameter bore portion of said anchoring member around its periphery.

6. A denture according to claim 1, wherein the outwardly tapered bore portion of said anchoring member which is directed away from the tooth extends up to the point of contact between the anchoring member and said pin.

7. A denture construction according to claim 1, including a plate engageable into a recess of the artificial tooth, said pin being threaded into said plate, said anchoring member having spherical formed outer walls, said plate being of substantially U-shaped cross section and having a skirt at its bottom portion formed of elastic material which is adapted to be anchored to the gums and which is curved complementarily to the outer walls of said anchoring member.

* * * * *